(12) United States Patent
Vautravers et al.

(10) Patent No.: US 9,765,003 B2
(45) Date of Patent: Sep. 19, 2017

(54) PROCESS FOR PRODUCING 2,6-DIMETHYL-5-HEPTEN-1-AL

(71) Applicant: BASF SE, Ludwigshafen (DE)

(72) Inventors: Nicolas Vautravers, Mannheim (DE); Joaquim H. Teles, Waldsee (DE); Ralf Pelzer, Fürstenberg (DE); Daniel Schneider, Frankenthal (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/308,755

(22) PCT Filed: May 4, 2015

(86) PCT No.: PCT/EP2015/059659
§ 371 (c)(1),
(2) Date: Nov. 3, 2016

(87) PCT Pub. No.: WO2015/169721
PCT Pub. Date: Nov. 12, 2015

(65) Prior Publication Data
US 2017/0183280 A1 Jun. 29, 2017

(30) Foreign Application Priority Data
May 5, 2014 (EP) .................................... 14167046

(51) Int. Cl.
C07C 45/28 (2006.01)
C07C 45/00 (2006.01)
C07C 45/82 (2006.01)

(52) U.S. Cl.
CPC ............ C07C 45/002 (2013.01); C07C 45/28 (2013.01); C07C 45/82 (2013.01)

(58) Field of Classification Search
CPC ........ C07C 45/002; C07C 45/28; C07C 45/82
USPC ...................................................... 568/485
See application file for complete search history.

(56) References Cited

U.S. PATENT DOCUMENTS 4,242,281 A 12/1980 Sprecker et al.
8,420,866 B2 4/2013 Teles et al.

FOREIGN PATENT DOCUMENTS

WO WO-2010076182 A1 7/2010

OTHER PUBLICATIONS

Burger, B., et al., "Semiochemicals of the Scarabaeidae. VII: Identification and Synthesis of EAD-Active Consituents of Abdominal Sex Attracting Secretion of the Male Dung Beetle, *Kheper subaeneus*", Journal of Chemical Ecology, vol. 28, No. 12, (2002), pp. 2527-2539.
Corma, A., et al., "A new, alternative, halogen-free synthesis for the fragrance compound Melonal using zeolites and mesoporous materials as oxidation catalysts", Journal of Catalysis, vol. 234, No. 1, (2005), pp. 96-100.
International Search Report for PCT/EP2015/059659 mailed Jul. 7, 2015.
Romanenko, E., et al., "Liquid-phase noncatalytic oxidation of monoterpenoids with nitrous oxide", Russian Chemical Bulletin, International Edition, vol. 56, No. 6, (2007), pp. 1239-1243.
Semikolenov, S., et al., "Liquid-phase noncatalytic butene oxidation with nitrous oxide", Russian Chemical Bulletin, International Edition, vol. 54, No. 4, (2005), pp. 948-956.
Starokon, E., et al., "Liquid Phase Oxidation of Alkenes with Nitrous Oxide to Carbonyl Compounds", Advanced Synthesis & Catalysis, vol. 346, Nos. 2-3, (2004), pp. 268-274.
Written Opinion and International Preliminary Report on Patentability for PCT/EP2015/059659 mailed Nov. 8, 2016.

*Primary Examiner* — Sikarl Witherspoon
(74) *Attorney, Agent, or Firm* — Drinker Biddle & Reath LLP

(57) ABSTRACT

The present invention relates to a process for producing 2,6-dimethyl-5-hepten-1-al, which comprises reacting 3,7-dimethyl-1,6-octadiene (dihydromyrcene, beta-citronellene) with $N_2O$ in a solvent or solvent mixture containing at least one solvent having a proton-donating functional group.

14 Claims, No Drawings

PROCESS FOR PRODUCING 2,6-DIMETHYL-5-HEPTEN-1-AL

CROSS-REFERENCE TO RELATED APPLICATIONS

This application is a national stage application (under 35 U.S.C. §371) of PCT/EP2015/059659, filed May 4, 2015, which claims benefit of European Application No. 14167046.3, filed May 5, 2014, both of which are incorporated herein by reference in their entirety.

The present invention relates to a process for producing 2,6-dimethyl-5-hepten-1-al, which comprises reacting 3,7-dimethyl-1,6-octadiene (dihydromyrcene, beta-citronellene) with $N_2O$ in a solvent or solvent mixture containing at least one solvent having a proton-donating functional group.

BACKGROUND OF THE INVENTION 2,6-Dimethyl-5-hepten-1-al is of great commercial interest as fragrance or as flavor due to its characteristic organoleptic properties. In particular, 2,6-dimethyl-5-hepten-1-al is used as additive in cosmetic preparations as well as in laundry and fabric detergents. Furthermore 2,6-dimethyl-5-hepten-1-al is a highly valuable intermediate for the production of other fragrances and flavors such as 6-hydroxy-2,6-dimethylheptanal and 6-methoxy-2,6-dimethylheptanal.

2,6-Dimethyl-5-hepten-1-al can be isolated from natural sources for instance from Java Citronella oil. However, the isolation of fragrances from natural sources is mostly expensive, their available amount is often limited and, on account of fluctuations in environmental conditions, they are also subject to variations in their content, purity etc.

Thus, a number of synthetic methods for the production of 2,6-dimethyl-5-hepten-1-al have been developed.

U.S. Pat. No. 4,242,281 for instance describes an industrial process for the production of racemic 2,6-dimethyl-5-hepten-1-al with a purity of 85% by a Darzens reaction, where 6-methyl-5-hepten-2-one is reacted with ethylchloroacetate in the presence of an alkali metal alkoxide such as sodium methoxide.

Corma et al., Journal of Catalysis, 2005, Vol. 234, pp. 96-100, describe a halogen-free synthesis strategy for the preparation of racemic 2,6-dimethyl-5-hepten-1-al involving the chemoselective oxidation of citral with $H_2O_2$ using a Sn-Beta zeolite based catalyst.

Burger et al., Journal of Chemical Ecology, 2002, Vol. 28, No. 12, pp. 2527-2539, describe the synthesis of (R)- and (S)-2,6-dimethyl-5-hepten-1-al starting from (R)- and (S)-3,7-dimethyl-1,6-octadiene, respectively. The synthesis comprises the selective epoxidation of the internal triple-substituted double bond of (R)- or (S)-3,7-dimethyl-1,6-octadiene using 3-chloroperbenzoic acid followed by the oxidation of the terminal double bond with ozone and the reduction of the thus obtained oxidation products with zinc to yield (R)- or (S)-2,6-dimethyl-5-hepten-1-al, respectively.

Since these processes have several technical and/or economical disadvantages, there is a need to find alternative synthetic processes, which allow the production of 2,6-dimethyl-5-hepten-1-al on industrial-scale in a more efficient way.

WO 2010/076182, describes a process for producing ketones, including the reaction of 1,1-disubstitued olefins with $N_2O$ in the presence of a solvent comprising at least one proton-supplying functional group.

Romanenko et ala, Russian Chemical Bulletin, International Edition, 2007, Vol. 56 (6), pp. 1239-1243, describe the chemoselective oxidation of limonene with $N_2O$ yielding 4-acetyl-1-methylcyclohexane as the major product.

Semikolenov et al., Russian Chemical Bulletin, International Edition, 2005, Vol. 54 (4), pp. 948-956, describe the oxidation of terminal olefins like for instance 1-butene with $N_2O$. In the case of 1-butene the aldehyde with one carbon atom less (propionaldehyde) is formed as a minor product with a selectivity of only 29%. Longer chain terminal olefins like 1-hexene and 1-octene behave similarly yielding the corresponding aldehydes with a selectivity of only 27% and 26%, respectively. In all cases the terminal olefins do not contain further oxidizable double bonds.

SUMMARY OF THE INVENTION

It is an object of the present invention to provide an improved process for the production of 2,6-dimethyl-5-hepten-1-al. The process should be simple and efficient to allow an economic production of 2,6-dimethyl-5-hepten-1-al.

It was surprisingly found that 2,6-dimethyl-5-hepten-1-al can be prepared in high selectivities by the oxidation of 3,7-dimethyl-1,6-octadiene with $N_2O$ in a solvent or solvent mixture containing at least one solvent having a proton-donating functional group.

Therefore, the present invention relates to a process for preparing 2,6-dimethyl-5-hepten-1-al, which comprises reacting 3,7-dimethyl-1,6-octadiene with $N_2O$ in a solvent or solvent mixture containing at least one solvent having a proton-donating functional group.

The processes for producing 2,6-dimethyl-5-hepten-1-al is simple and efficient, starting from cheap and readily available 3,7-dimethyl-1,6-octadiene. By using the process according to the present invention, 2,6-dimethyl-5-hepten-1-al can be provided without difficulty on industrial scales.

DETAILED DESCRIPTION 2,6-dimethyl-5-hepten-1-al is a compound of the following formula (I),

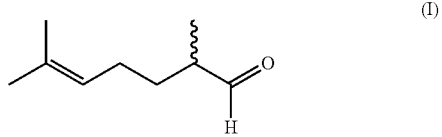

which may have (R)- or (S)-configuration at its 2-position.

According to the present invention, the term "2,6-dimethyl-5-hepten-1-al" refers to both the (2R)- and the (2S)-stereoisomer of 2,6-dimethyl-5-hepten-1-al and to mixtures of these stereoisomers.

Using the process of the present invention, 2,6-dimethyl-5-hepten-1-al is typically obtained either in the form of a racemic mixture or in the form of a mixture of its (2R/2S)-stereoisomers, in which either the (2R)-isomer or the (2S)-isomer is present in excess, depending on whether the starting material 3,7-dimethyl-1,6-octadiene is applied as a racemic mixture or in form of its pure (3R)- or (3S)-stereoisomer.

According to the present invention, the oxidation is carried out in the presence of a solvent or a solvent mixture containing at least one solvent having a proton-donating functional group.

The solvent having a proton-donating functional group may be selected from any substances, which have a proton-donating functional group and do not react with $N_2O$ under the reaction conditions. Proton-donating functional groups are those functional groups having a hydrogen atom, which is attached to a heteroatom, in particular to O, S or N. Examples of such functional groups include COOH, OH or NH. The solvent may carry one or more, e.g. 1, 2 or 3, of such functional groups.

Examples of suitable solvents having a COOH group are unsubstituted or substituted carboxylic acids having 1 to 20 carbon atoms and one or two carboxyl group, for example acetic acid, propionic acid, butyric acid, isobutyric acid, pivalic acid, valeric acid, hexanoic acid, heptanoic acid, octanoic acid, capric acid, lauric acid, myristic acid, stearic acid, succinic acid, glutaric acid, adipic acid, suberic acid or pimelic acid, and aromatic carboxylic acids having one or two carboxyl groups, for example benzoic acid, ortho-toluic acid, meta-toluic acid, para-toluic acid, phthalic acid, isophthalic acid or terephthalic acid.

Examples of suitable solvents having an OH group are water, aliphatic alcohols, for example methanol, ethanol, 1-propanol, 2-propanol, 1-butanol, 2-butanol, isobutanol, tert.-butanol, 1-pentanol, 2-pentanol, isopentanol, tert-pentanol, cyclopentanol, 3-methyl-2-butanol, 1-hexanol, 2-hexanol, 3-hexanol, 2-methylpentanol, cyclohexanol, 1-heptanol, isoheptanol, 1-octanol, 2-octanol, 2-ethylhexanol, 1-nonanol, isononanol, 1-decanol, 2-propyiheptanol, 2-propyl-3-methyl-pentanol, 1-undecanol, isoundecanol, 1-dodecanol, 2-butyloctanol, 2-butyl-3-methylheptanol, 1-tridecanol, 1-tetradecanol, 1-hexadecanol, 1-octadecanol or 1-icosanol, aliphatic diols having 2 to 20 carbon atoms, for example ethylene glycol, 1,2-propanediol, 1,3-propanediol, 1,2-butanediol, 2,3-butanediol, 1,2-pentanediol, 1,5-pentanediol, 1,6-hexanediol, 1.8-octanediol, 1,10-decanediol, 1,12-dodecanediol, 1,18-octadecanediol or diethylene glycol, aliphatic triols having 3 to 20 carbon atoms, for example glycerol or 1,2,4-butanetriol, aliphatic polyols having 4 or more OH groups and 4 to 20 carbon atoms, for example threitol or sorbitol, phenol and substituted phenols, for example, para-cresol, 2,4-xylenol, 2-methoxyphenol or 4-methoxyphenol.

Examples of suitable solvents having a NH group are ammonia, primary or secondary aliphatic amines having 1 to 30 carbon atoms, for example methylamine, ethylamine, propylamine, isopropylamine, butylamine, isobutylamine, tert.-butylamine, pentylamine, hexylamine, octylamine, 2-ethylhexylamine, 2-propyheptylamine, dimethylamine, methylethylamine, diethylamine, dipropylamine, diisopropylamine, dibutylamine, dipentylamine, dihexylamine, pyrrolidine or piperidine, aliphatic di- and polyamines having 2 to 20 carbon atoms, for example 1,2-ethylenediamine, 1,3-diaminopropane, N,N-dimethyl-1,3-diaminopropane, bis(-2-aminoethyl)amine, 1,4-diaminobutane and piperazine, aromatic amines, for example aniline, N-methylaniline or toluidine, and primary or secondary amides, for example formamide, acetamide, N-methylacetamide, 2-pyrrolidone or caprolactam.

According to the present invention, the solvent having a proton-donating functional group is also selected from compounds which simultaneously have an OH group and a COOH group.

Examples of suitable solvents having an OH group and a COOH group are alpha hydroxy acids, for example glycolic acid, lactic acid, malic acid, tartaric acid, citric acid or mandelic acid and beta hydroxy acids, for example propanoic acid, beta hydroxy butyric acid or salicilic acid.

According to the present invention, the solvent having a proton-donating functional group is also selected from compounds which simultaneously have an OH group and a NH group.

Examples of suitable solvents having an OH group and a NH group are ethanolamine, 1-amino-2-propanol, 1-amino-2-methyl-2-propanol, 2-amino-2-methyl-1-propanol, diethanolamine and dipropanolamine.

In a preferred embodiment, the solvent having a proton-donating functional group is selected from aliphatic alcohols as defined above.

In a particular preferred embodiment, the solvent having a proton-donating functional group is selected from $C_1$-$C_4$-alkanols, such as methanol, ethanol, 1-propanol, 2-propanol, 1-butanol, 2-butanol, isobutanol and tert.-butanol.

In an especially preferred embodiment, the solvent having a proton-donating functional group is selected from methanol.

According to the present invention, the oxidation can be carried out in a solvent mixture comprising at least one solvent having a proton-donating functional group, as defined above, and optionally at least one further solvent, which does not have a proton-donating functional group.

It is preferred that the optional further solvent having no proton-donating functional group is an organic solvent, which is inert under the reaction conditions. Preferred inert organic solvents are, by way of example, aliphatic or alicyclic hydrocarbons, in particular alkanes and cycloalkanes having 5 to 12 carbon atoms, halogenated aliphatic hydrocarbons, and aromatic and substituted aromatic hydrocarbons and aliphatic or alicyclic ethers. Examples of inert solvents are aliphatic hydrocarbons, such as pentane, hexane, heptane, ligroin or petrol ether, alicyclic hydrocarbons, such as cyclopentane, cyclohexane or cycloheptane, halogenated hydrocarbons, such as dichloromethane, trichloromethane, tetrachloromethane or 1,2-dichloroethane, aromatics, such as benzene, toluene, xylenes, chlorobenzene, dichlorobenzenes, ethers such as methyl-tert.-butylether, dibutyl ether, tetrahydrofurane, 1,4-dioxane, 1,2-dimethoxyethane and mixtures thereof.

In general, the amount of solvent having a proton-donating functional group is present in an amount of at least 6 mol or at least 8 mol, e.g. from 6 to 40 mol, in particular from 8 to 17 mol, especially from 9 to 13 mol, per 1 mol of 3,7-dimethyl-1,6-octadiene.

Typically, the concentration of 3,7-dimethyl-1,6-octadiene in the solvent or solvent mixture is from 10 to 40% by weight, preferably from 20 to 35% by weight and in particular from 25 to 33% by weight, based on the total weight of solvent or solvent mixture and 3,7-dimethyl-1,6-octadiene.

With regard to the selectivity of the formation of 2,6-dimethyl-5-hepten-1-al it is found to be beneficial, if the reaction conditions and in particular the amount of $N_2O$, the reaction pressure, reaction temperature and the reaction time is chosen such that the conversion of 3,7-dimethyl-1,6-octadiene is in the range of from 2 to 40%, preferably in the range of from 2,5 to 30%, in particular in the range of from 3 to 20%.

To this end, 3,7-dimethyl-1,6-octadiene is heated together with the solvent or solvent mixture, as defined above, in the presence of $N_2O$. To increase the solubility of $N_2O$ in the liquid phase, the reaction is preferably performed at elevated pressure.

The reaction is in particular performed at a pressure, in particular at a N₂O pressure, in the range of 5 to 400 bar, preferably in the range of 10 to 350 bar, especially in the range from 15 to 300 bar.

Typically, the reaction is performed without adding a catalyst.

The oxidation reaction is usually carried out in the temperature range from 100 to 300° C., preferably from 130 to 290° C., in particular in the range from 150 to 280° C., The oxidation reaction can take place in the absence of or in the presence of an inert gas, either added on purpose or contained in the N₂O used. The expression inert gas generally means a gas, which under the prevailing reaction conditions does not enter into any reactions with the starting materials, reagents, or solvents participating in the reaction, or with the resultant products. Examples of inert gases are carbon dioxide, nitrogen and argon. It is preferable that the amount of inert gas is less than 20% of the amount of N₂O used.

In particular, the molar ratio of N₂O to 3,7-dimethyl-1, 6-octadiene used in the oxidation reaction is in the range of 1:20 to 4:1, preferably in the range of 1:15 to 3:1, in particular in the range of 1:10 to 1:1.

The oxidation can be designed to take place either continuously or batchwise, preference being given here to the continuous design of the process. The batchwise oxidation can be conducted in a reaction apparatus conventionally used for this purpose, e.g. a stirred reactor. It is preferable that the oxidation according to the present invention is carried out continuously, e.g. in a tube reactor or in a cascade of at least three back-mixed reactors. The reactors can be operated nearly isothermally or nearly adiabatically. In the case of continuously operated reactors the beta-citronellene (3,7-dimethyl-1,6-octadiene), the solvent and the N₂O, optionally containing an inert gas, are fed as liquid streams to the reactor. Preferably, the temperature, pressure and composition of the feed is chosen in such a way that the mixed feed stream at the reactor entrance is liquid (i.e. does not have a gaseous phase) and homogeneous (no separation into two liquid phases).

The process of the present invention provides 2,6-dimethyl-5-hepten-1-al in good selectivity. Surprisingly, N₂O preferentially reacts with the mono-substituted double bond of 3,7-dimethyl-1,6-octadiene under cleavage of the C=C bond, giving the corresponding aldehyde as the major product.

Generally, the crude product mixture obtained by the process according to the present invention may comprise further reaction products. In particular, the crude product mixture may contain, in addition to the main product of formula (I), one or more further products of the general formulae (II) to (VIII).

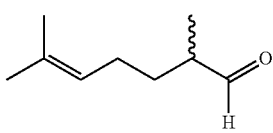
(I)

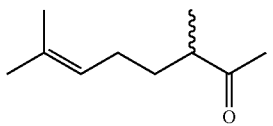
(II)

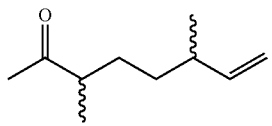
(III)

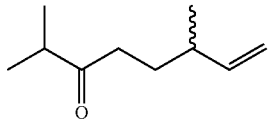
(IV)

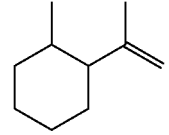
(V)

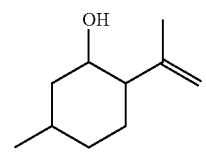
(VI)

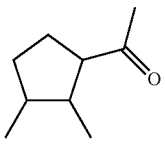
(VII)

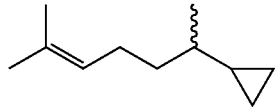
(VIII)

The process of the present invention may further comprise the purification of 2,6-dimethyl-5-hepten-1-al, e.g. by distillation.

Preferred distillation devices for the purification of 2,6-dimethyl-5-hepten-1-al are for example distillation columns, such as tray columns optionally equipped with bubble cap trays, sieve plates, sieve trays, packages or filler materials, or spinning band columns, such as thin film evaporators, falling film evaporators, forced circulation evaporators, Sambay evaporators, etc. and combinations thereof. Especially preferred distillation devices for the purification of 2,6-dimethyl-5-hepten-1-al are distillation columns, in particular spinning band columns and packed columns.

After distillative purification 2,6-dimethyl-5-hepten-1-al can typically be obtained in high purity, e.g. in a purity of at least 80%. Generally, 2,6-dimethyl-5-hepten-1-al is obtained as a mixture of its (2R)- and (2S)-stereoisomers as defined above.

The starting material 3,7-dimethyl-1,6-octadiene (dihydromyrcene, beta-citronellene) is commercially available in the form of its pure enantiomers, or as a racemic mixture.

EXAMPLES

I) Gas Chromatographic Analysis:
GC-System and Separation Method:
GC-system: Agilent 5890 Series II;
GC-Column: HP-5 (30 m (Length), 0.25 mm (ID), 0.25 μm (Film));
Temperature program: 40° C. for 6 minutes, 40° C. to until 250° C. in 8° C./min, II) Production Examples:

Example II.1

Oxidation of (3R)-3,7-dimethyl-1,6-octadiene ((−)-beta-dihydromyrcene) in methanol at 220° C. with N$_2$O (40 bar) in a batch autoclave A 300 mL autoclave is charged with 33.0 g (−)-beta-dihydromyrcene (91 wt.-%, obtained from Aldrich Chemicals) in 67.0 g methanol and flushed 3 times with N$_2$ (50 bar). The vessel is then pressurized with N$_2$O (40 bar) at room temperature. The magnetic stirring is turned on and the autoclave heated to the reaction temperature (220° C.) for 3 hours. During reaction the pressure in the autoclave was about 75-80 bar. After cooling to room temperature and slow depressurization, the solution was analyzed by quantitative GC using 1,4-dioxane as the internal standard. The conversion of (−)-beta-dihydromyrcene was 8% and the selectivities of (I), (II), (III), (IV), (V), (VI), (VII) and (VIII) where found to be 51%, 6%, 6%, 3%, 2%, 3%, 2% and 2% respectively.

Example II.2

Oxidation of (3R)-3,7-dimethyl-1,6-octadiene ((−)-beta-dihydromyrcene) in methanol at 220° C. (isothermal) with N$_2$O (270 bar) in continuous mode The reactor used was a custom built reactor from Heatric Division of Meggitt UK Ltd microstructured reactor built of SS316L stainless steel plates with etched channels having a radius of 1.2 mm and diffusion bonded to form a reactor with a net reaction volume of 0.5 L. The reactor is thermostated by circulating a Marlotherm oil whose temperature at the reactor entrance is regulated at 220° C. with a suitable thermostat through intertwined heat-transfer plates (ca. ⅓ of the plates are for the heat-transfer medium and ⅔ of the plates are for the reactants). The two reactor feed streams consists of (−)-beta-dihydromyrcene (88 wt.-% purity, obtained from Wanxiang) dissolved in methanol (29 wt-% solution) (flow rate: 675 g/h) and liquid N$_2$O (flow rate: 45 g/h) and are fed by using suitable high-pressure metering pumps. The experiments were performed in a continuous manner. The pressure is kept constant at 270 bar by a pressure regulating valve at the reactor exit. The reactor effluent after depressurization was collected, weighed and analyzed with quantitative GC using 1,4-dioxane as the internal standard. The conversion of (−)-beta-dihydromyrcene was 3% and the selectivities of (I), (II), (III), (IV), (V), (VI), (VII) and (VIII) where found to be 40%, 12%, 15%, 8%, 3%, 3%, 3% and 2% respectively.

III) Purification:

The crude reaction mixture of II.1) was purified by distillation using a spinning band column giving racemic 2,6-dimethyl-5-hepten-1-al with a purity of 89% as a clear colorless liquid.

IV) Scent Strip Tests:

To confirm the organoleptic identity of the purified 2,6-dimethyl-5-hepten-1-al, obtained in example III), scent strip tests were performed and compared with commercially available 2,6-dimethyl-5-hepten-1-al.

For this purpose strips of absorbent paper were dipped into solution containing 1 to 10 wt.-% 2,6-dimethyl-5-hepten-1-al in ethanol. After evaporation of the solvent (about 30 sec.) the scent impression was olfactorically evaluated by a trained perfumer.

Results of the scent strip tests:

Product of example III) with 89% purity (clear, colorless liquid):

| Time elapsed | Odor impression |
| --- | --- |
| <1 min. | citron-like, reminding on citronellal, waxy, harsh |
| 10 min. | citron-like, reminding on citronellal, waxy, harsh |
| 30 min. | citron-like, reminding on citronellal |
| 1 h | weakly dusty |
| 24 h | almost odorless |

The invention claimed is:

1. A process for preparing 2,6-dimethyl-5-hepten-1-al, which comprises reacting 3,7-dimethyl-1,6-octadiene with N$_2$O in a solvent or solvent mixture containing at least one solvent having a proton-donating functional group.

2. The process of claim 1, wherein the solvent having a proton-donating functional group is an aliphatic alcohol.

3. The process of claim 1, wherein the solvent having a proton-donating functional group is a $C_1$-$C_4$-alkanol.

4. The process of claim 1, wherein the solvent having a proton-donating functional group is methanol.

5. The process of claim 1, wherein the amount of solvent having a proton-donating functional group is present in an amount of 6 to 40 mol per 1 mol of 3,7-dimethyl-1,6-octadiene.

6. The process of claim 1, wherein the concentration of 3,7-dimethyl-1,6-octadiene in the solvent or solvent mixture is from 10 to 40% by weight, based on the total weight of solvent or solvent mixture and 3,7-dimethyl-1,6-octadiene.

7. The process of claim 1, wherein the reaction of 3,7-dimethyl-1,6-octadiene with N$_2$O is performed until the conversion of 3,7-dimethyl-1,6-octadiene is in the range of from 3 to 20%.

8. The process of claim 1, wherein the, reaction is performed at a pressure in the range of 5 to 400 bar.

9. The process of claim 1, wherein the molar ratio of N$_2$O to 3,7-dimethyl-1,6-octadiene is in the range from 1:20 to 4:1.

10. The process of claim 1, wherein the molar ratio of N$_2$O to 3,7-dimethyl-1,6-octadiene is in the range from 1:10 to 1:1.

11. The process of claim 4, wherein the molar ratio of N$_2$O to 3,7-dimethyl-1,6-octadiene is in the range from 1:10 to 1:1 and the reaction is performed at a pressure in the range of 5 to 400 bar and a temperature is in the range of 100 to 300° C.

12. The process of claim 1, wherein the reaction temperature is in the range of 100 to 300° C.

13. The process of claim 1, wherein 3,7-dimethyl-1,6-octadiene is reacted with N$_2$O in a continuous manner.

14. The process of claim 1, further comprising the purification of the reaction mixture by distillation.

* * * * *